United States Patent [19]
van der Burgt

[11] 3,973,235
[45] Aug. 3, 1976

[54] DEVICE FOR THE DETECTION OF AN ACOUSTIC IMAGE

[75] Inventor: Cornelis Martinus van der Burgt, Eindhoven, Netherlands

[73] Assignee: U.S. Philips Corporation, New York, N.Y.

[22] Filed: Apr. 15, 1974

[21] Appl. No.: 461,017

[30] Foreign Application Priority Data
Apr. 24, 1973 Netherlands.................... 7305667

[52] U.S. Cl.............................. 340/5 MP; 73/67.7; 313/369
[51] Int. Cl.²........................................ H01J 31/495
[58] Field of Search.............. 340/5 MP, 5 H, 13 R; 313/369; 73/67.5 H, 67.7, 67.8 R, 67.8 S, 67.9

[56] References Cited
UNITED STATES PATENTS
3,325,777   6/1967   Fyler.................. 340/5 MP
3,622,825   11/1971   Bennett............................. 313/369

Primary Examiner—Richard A. Farley
Attorney, Agent, or Firm—Frank R. Trifari; Bernard Franzblau

[57] ABSTRACT

Apparatus for the detection of an acoustic image by means of an election tube including a face plate and an electronically scanned transducer made of a thin foil of polymer material whose acoustic wave velocity of propagation is less than 1.8 that of a liquid imaging medium. The face plate also is made of a polymer material having a velocity of propagation less than 1.8 that of said liquid. Preferably, the transducer foil is much thinner than the face plate and has a thickness approximately 0.5 times the acoustic wavelength.

9 Claims, 1 Drawing Figure

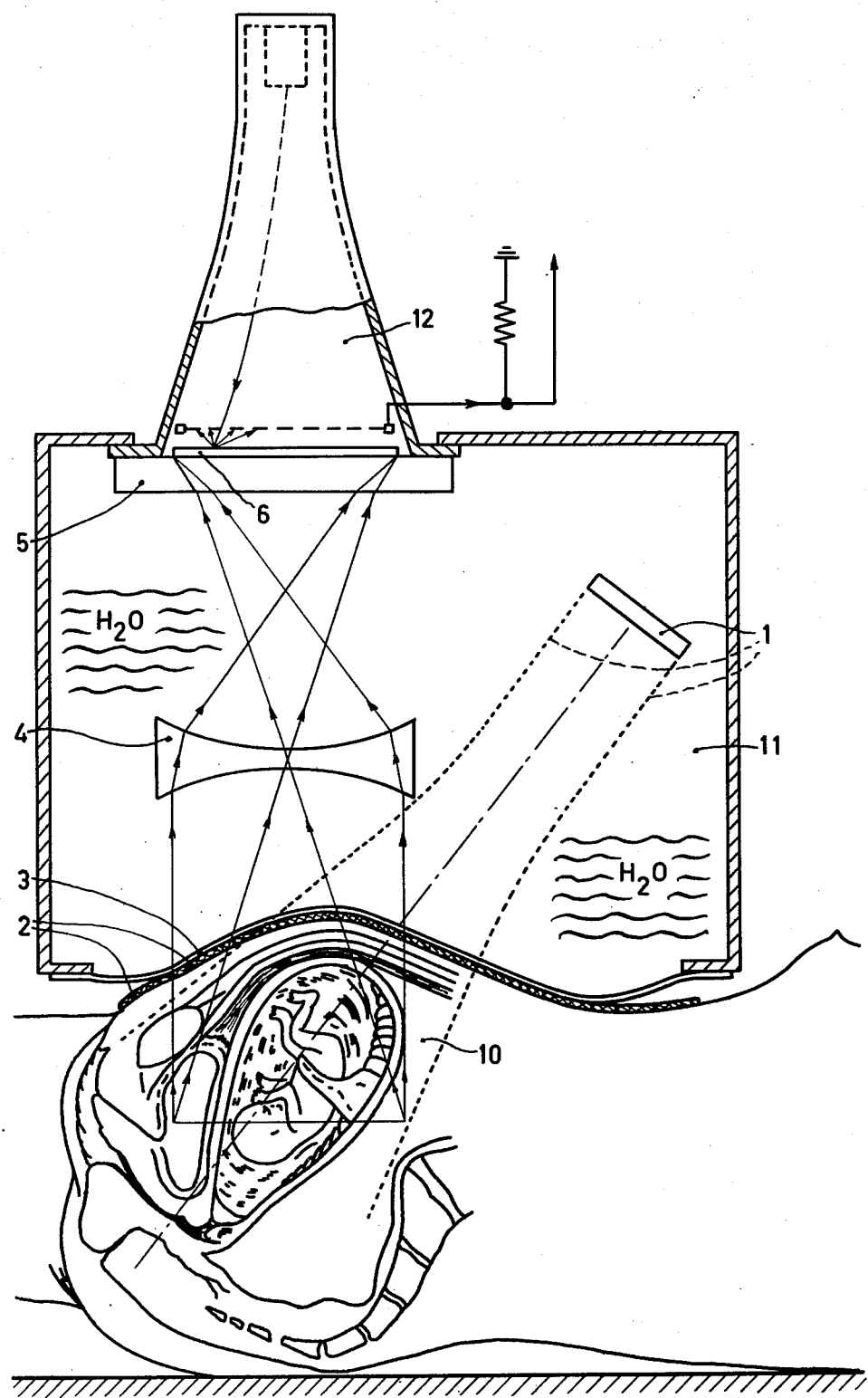

DEVICE FOR THE DETECTION OF AN ACOUSTIC IMAGE

The invention relates to a device for the detection of an acoustic image, the acoustic waves being imaged via acoustic imaging means, which comprise at least a liquid medium and an acoustic lens, onto a transducer, which is incorporated in an electron tube, for converting acoustic vibrations into a charge image which can be scanned electronically, the transducer being separated from the liquid medium by a non-piezoelectric face plate which is mounted on the electron tube, which face plate should be capable of withstanding a difference in atmospheric pressure.

Such a device is, for example, used in industry to detect internal flaws in moving or stationary workpieces, in underwater investigations where obstacles or lost objects are to be traced or, for example a drilling site at the bottom of the sea is to be surveyed, in hospitals for ultrasonic diagnosis, for example for the localisation of tumors in the brain, breasts or uterus or in observing the cardiac action. In all these instances a visual display with at least 25 complete images per second is aimed at, so that rapidly moving objects or object portions (pulsating arteries, cardiac valve, foetus) can also be observed accurately and can be recorded on film or video tape.

For this purpose it is known to expose the object under test or to irradiate said object with acoustic waves (in this respect the term acoustic denotes both audible and ultrasonic sound waves, for example up to a frequency of 10 MHz). After being focussed the acoustic waves then impinge on a so-called Sokolov tube, which incorporates said transducer, where a charge image which corresponds to the acoustic images is formed, which can subsequently be scanned with an electron beam.

A drawback of the Sokolov tube is that the piezoelectric transducer, which at the same time forms a wall of the tube, must be very thin to attain the highest sensitivity and the highest resolving power for the acoustic waves to be detected. In order to obviate said drawback it has been proposed to provide the tube with an external face plate so that it is better able to withstand the difference in pressure between the inside and outside of the tube, thus enabling the use of cheap, large screens. The invention is based on the following considerations:

1. The minimum size of a picture element that can still be resolved approximately equals the thickness of the piezoelectric transducer plate of the Sokolov tube, said thickness preferably being approximately equal to half an acoustic wavelength. When using a monocrystalline quartz in X-cut this means a thickness of approximately 2 and 1 mm respectively for acoustic waves having a frequency of approximately 1½ and 3 MHz respectively. The resolving power is then still inadequate.

2. A quartz plate of the said small thickness is only capable of withstanding by itself a pressure difference of 1 atmosphere if it has a small diameter. For piezoelectric materials other than quartz the maximum permissible diameter is even smaller. A much greater diameter is required, i.e. a high linear aperture.

3. Acoustic rays which reach the piezo-electric transducer surface at an angle of incidence greater than 3° to 4° do not exclusively produce the desired thickness vibrations in the transducer, but bending or surface waves will also propagate along the plate surface, as a result of which the image is disturbed. This "angular aperture" is unsatisfactorily low.

The invention is characterized by the following combination:

a. the face plate is made of a polymer having a velocity of propagation for acoustic waves whose ratio to that of the liquid is smaller than 1.8.

b. the thickness of the transducer is appreciably smaller than that of the face plate and equals approximately 0.5 times the acoustic wavelength;

c. the transducer is also made of a polymer, viz. a polymer with remanent electrical polarization, and is applied to the face plate as a thin film; and d. the velocity of propagation for acoustic waves of the transducer material in proportion to that of the liquid is also smaller than 1.8.

Owing to the provision of the face plate the problem which is caused by said atmospheric pressure difference reduces the provision of an element which is adapted as well as possible to the further acoustic arrangement. Generally, water will be selected as a liquid medium and the material of the screen plate, provided that its velocity of propagation is not too high relative to that of water, will only cause a slight diffraction of the acoustic waves at the interface between liquid and screen plate. Moreover, possible bending or surface waves should be damped out as rapidly as possible so as to ensure that the acoustic image formed on the transducer is blurred to the least extent. Both requirements are met by a polymer having an acoustic velocity of propagation which is not too high, such as polyethylene or polystyrene.

As the transducer is considerably thinner, for example by a factor of 50, than the screen plate and both have substantially the same velocity of sound, only a slight disturbing effect will occur at the interface between screen plate and transducer so that the highest possible resolving power is maintained. In this respect it is also of importance that when using said materials for the face plate and the transducer undesired surface waves are damped out.

A particularly suitable material for such a transducer is polyvinylidene fluoride in the form of a stretched and polarised foil. At a high temperature, for example 100° to 150°C such a foil can mechanically be stretched uniaxially or biaxially up to 2 to 3 times its original dimensions. Simultaneously or later the stretched foil is subjected to a strong electric field, for example with a field strength of 300 to 1000 kV/cm, for approximately 1 hour at 50° to 150°C, so that a powerful remanent electrical polarisation persists in the foil after it has been cooled down to room temperature at approximately the same field strength. It is of particular importance that such a foil readily adapts itself to the shape of the face plate. To this end the face plate may, for example, be curved outwards slightly so as to be better able to withstand said pressure difference, the foil readily following this curved shape.

Compared with the use of said quartz materials for the transducer it appears that the resolving power is improved in accordance with the ratio of the velocities of sound in quartz and in polyvinylidene fluoride respectively, i.e. by a factor of more than 2.

The FIGURE shows an embodiment of the invention.

The ultrasonic sound source is formed by a quartz half wavelength oscillator 1 whose vibrations irradiate an object 10. This object is in direct acoustical contact with a space 11 which is closed by a flexible rubber diaphragm 3 and which is in engagement with the object 10 via a viscous coupling layer 2. The space 11 is filled with a liquid, for example, water, and furthermore comprises an acoustic lens 4, for example Perspex, by which the acoustic vibrations can be imaged onto a transducer 6, which is incorporated in an electron tube 12, i.e. is mounted on a face plate 5 which is capable of withstanding the difference in pressure between the liquid in the space 11 and the vacuum inside the tube 12. If necessary, the face plate may previously be curved outwardly so that it straightens after evacuation of the tube 12. The thin transducer 6, which is formed by a foil, can readily follow the variations of the shape of the plate 5. The advantage of this is that the screen plate may be slightly thinner.

By imposing the requirements outlined above on the material of the face plate 5, for example polystyrene or polyethylene, and of the transducer 6, for example polyvinylidene fluoride, a high resolving power in combination with a screen of reasonably large dimensions is obtained. The electrical charge image obtained on a transducer is scanned in the usual manner with the aid of an electron beam and converted into an electrical signal, which in its turn can be recorded either on a film or by means of a video recorder.

What is claimed is:

1. An electron vacuum tube comprising a face plate which is capable of withstanding the pressure difference between the inside and outside of the tube and which is made of a polymer material having a low velocity of acoustic propagation, a transducer for converting an acoustic image into a corresponding electric charge image and located inside of the tube adjacent the face plate, said transducer being formed of a stretched thin foil made of a polymer material which also has a low velocity of acoustic propagation and has a remanent electrical polarization, the velocity of acoustic propagation of the face plate and transducer material each being less than 1.8 times that of a liquid medium used to image the acoustic wave image onto the transducer via said face plate, the transducer being thinner than the face plate and approximately 0.5 times the acoustic wavelength, and means for electronically scanning the transducer charge image.

2. An electron tube as claimed in claim 1, characterized in that at least prior to evacuation of the tube the face plate has an outwardly curved shape so as to be better able to withstand said pressure difference.

3. Apparatus for the detection of an acoustic image comprising, an electron vacuum tube including a non-piezoelectric face plate, a transducer for converting an acoustic image into a charge image and means for electrically scanning the transducer charge image, acoustic imaging means including a liquid medium and an acoustic lens for imaging acoustic waves of said image onto the transducer, the transducer being separated from the liquid medium by the electron tube face plate which is capable of withstanding the difference in pressure that exists between the vacuum inside the tube and the surrounding liquid, wherein the face plate is made of a polymer material having a velocity of propagation for acoustic waves which in relation to that of the liquid is less than 1.8, the transducer comprises a thin foil of polymer material applied to the face plate and is appreciably thinner than the face plate and has a thickness approximately 0.5 times the acoustic wavelength, and the velocity of propagation for acoustic waves in the transducer material in relation to that of the liquid is less than 1.8.

4. Apparatus as claimed in claim 3 wherein the transducer comprises polyvinylidene fluoride having a remanent electric polarization.

5. Apparatus for the detection of an acoustic image of an object comprising, a liquid medium for the propagation of acoustic wave energy, a source of acoustic wave energy for irradiating the object via the liquid medium, an electron tube having a non-piezoelectric face plate the outer surface of which is adjacent the liquid medium and the inner surface supporting a transducer for converting acoustic energy into an electric charge image, means for focusing the acoustic image reflected from the object onto said transducer via the liquid medium and the tube face plate, said electron tube including means for electronically scanning a charge image formed on the transducer, wherein the improvement comprises a face plate made of a polymer material having a velocity of propagation for acoustic waves which is less than 1.8 the acoustic wave velocity of propagation of the liquid medium, a transducer made of polymer material whose velocity of propagation for acoustic waves is less than 1.8 the acoustic wave velocity of propagation of the liquid medium, the thickness of the transducer being less than that of the face plate and approximately 0.5 times the acoustic wavelength.

6. Apparatus as claimed in claim 5 wherein the transducer comprises a thin film of polymer material having a remanent electric polarization.

7. Apparatus as claimed in claim 5 wherein the transducer material is polyvinylidene fluoride.

8. Apparatus as claimed in claim 5 wherein the face plate is made of a material selected from the group of materials consisting of polystyrene and polyethylene materials.

9. Apparatus as claimed in claim 5 wherein the thickness of the face plate is approximately 50 times greater than that of the transducer and both have approximately the same velocity of propagation for acoustic waves.

* * * * *